(12) United States Patent
Sharab et al.

(10) Patent No.: US 11,974,885 B2
(45) Date of Patent: May 7, 2024

(54) NEUROPILOT MANUAL NEURAL NAVIGATION DEVICE

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Momen Ahmad Sharab, Riyadh (SA); Balgees Abdullah Ajlan, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 760 days.

(21) Appl. No.: 17/061,066

(22) Filed: Oct. 1, 2020

(65) Prior Publication Data
US 2022/0104906 A1   Apr. 7, 2022

(51) Int. Cl.
*A61B 90/11* (2016.01)
*A61B 17/34* (2006.01)
*A61B 90/00* (2016.01)
*A61B 90/10* (2016.01)
(Continued)

(52) U.S. Cl.
CPC ....... *A61B 90/11* (2016.02); *A61B 2017/3405* (2013.01); *A61B 2090/067* (2016.02); *A61B 2090/0807* (2016.02); *A61B 2090/103* (2016.02); *A61M 25/06* (2013.01); *A61M 27/006* (2013.01)

(58) Field of Classification Search
CPC . A61B 90/11; A61B 90/13; A61B 2017/3405; A61B 2017/3407; A61B 2017/3409; A61B 2017/3425; A61B 2017/3427; A61B 2017/345; A61B 2017/3452
See application file for complete search history.

(56) References Cited

U.S. PATENT DOCUMENTS 4,058,114 A     11/1977  Soldner
4,613,324 A *    9/1986  Ghajar .............. A61B 17/3403
                                                606/108
(Continued)

FOREIGN PATENT DOCUMENTS

CN          105877816 A        8/2016

OTHER PUBLICATIONS

Schaumann, et al. ; Guided Application of Ventricular Catheters (GAVCA)—multicentre study to compare the ventricular catheter position after use of a catheter guide versus freehand application: study protocol for a randomised trail ; Schaumann and Thomale Trials 2013 ; 9 Pages.

*Primary Examiner* — Martin T Ton

(57) ABSTRACT

A device suitable for guiding a trajectory of a surgical shunt or needle comprising two protractors on a curved frame configured to fit over, or attach to, the skull of a patient, wherein the two protractors are respectively oriented in a circular dimension and anterior-posterior/medio-lateral directions. A method for using the device to guide a surgical needle, probe, shunt or other instrument during surgery.

17 Claims, 12 Drawing Sheets

(51) Int. Cl.
*A61M 25/06* (2006.01)
*A61M 27/00* (2006.01)

(56) References Cited

U.S. PATENT DOCUMENTS

| | | | | |
|---|---|---|---|---|
| 5,201,742 | A * | 4/1993 | Hasson | A61B 90/11 |
| | | | | 606/1 |
| 2002/0049451 | A1* | 4/2002 | Parmer | A61B 90/11 |
| | | | | 606/108 |
| 2008/0109026 | A1* | 5/2008 | Kassam | A61B 17/00234 |
| | | | | 600/101 |
| 2011/0190787 | A1* | 8/2011 | Sahni | A61B 90/11 |
| | | | | 606/130 |
| 2013/0066192 | A1 | 3/2013 | Sarvestan et al. | |
| 2013/0197534 | A1* | 8/2013 | Lauderbaugh | A61B 17/3403 |
| | | | | 606/108 |
| 2016/0022308 | A1 | 1/2016 | Rohling | |
| 2017/0007349 | A1* | 1/2017 | Solar | A61B 34/20 |
| 2017/0296202 | A1* | 10/2017 | Brown | A61B 34/10 |
| 2018/0125528 | A1* | 5/2018 | Page | A61B 17/34 |
| 2019/0060673 | A1* | 2/2019 | McKenna | G01T 1/02 |

* cited by examiner

Axial

Coronal

Sagittal

NEUROPILOT MANUAL NEURAL NAVIGATION DEVICE

BACKGROUND OF THE INVENTION

Field of the Invention

The invention pertains to the field of neurosurgery, specifically to a neuronavigation device (guide) which can be used manually in urgent and elective neurosurgical procedures.

Description of Related Art

Many neurosurgical procedures require probing or insertion of a needle or other surgical instrument inside of the skull into the brain. Examples of these procedures include tissue biopsies, drainage of fluids, ablation for cancer treatment, catheterization and drug delivery.

Preferably, these procedures are planned in advance using data from CT (CAT) or MRI imaging and are performed with intraoperative imaging to accurately guide a probe or other device toward a target site. Such guidance is especially important when a target site is in a sensitive location or deep within the brain. Sometimes, establishing an accurate trajectory blindly by the surgeon may be inadequate to guide the probe or other instrument and to recognize when it has reached the target site. Thus, during such procedures it is advantageous to conduct the surgery under the guidance of real-time intraoperative imaging of the target site and surrounding areas (neuronavigation) to improve the safety and accuracy of the procedure.

Neuronavigation is becoming one of the fundamental tools in neurosurgery. It is a set of computer-assisted technologies used by neurosurgeons to guide or "navigate" within the confines of the skull. Modern neuro-imaging technologies such as computed tomography (CT) and magnetic resonance imaging (MM) make possible real-time quantitative spatial fusion of images of the patient's brain with a created "fiducial coordinate system" or reference anatomical landmarks for the purpose of guiding the surgeon's instrument or probe to a selected target in the brain.

Examples of the most common neurosurgical procedures which can be performed under neuronavigation involve brain tumor biopsies, abscess drainage, ventriculoperotoneal (VP) shunts, and the placement of external ventricular drains (EVD) when the ventricles are slit or has a distorted anatomy. It is essential in brain biopsies especially for deep seated lesions or during abscess drainage. Abscess drainage is almost always an acute emergency that requires urgent evacuation. These procedures are often lifesaving because they reduce intercranial pressure (ICP) and halt potential tonsillar herniation. In brain trauma, where anatomy is distorted and there's a need for multiple passes to access the ventricles, neuronavigation was associated with a higher accuracy in EVD placement (94.7%) and in a significantly lower number of passes in severe TBI patients; AlAzri A, Mok K, Chankowsky J, Mullah M, Marcoux J. Placement accuracy of external ventricular drain when comparing freehand insertion to neuronavigation guidance in severe traumatic brain injury. Acta neurochirurgica. 2017; 159(8): 1399-411. Epub 2017/05/31. Neuronavigation enhances accuracy and helps guide surgical decisions both preoperatively and intraoperatively.

Unfortunately, the advantages of sophisticated neuronavigation are not always available, for example, suitable equipment is often not available in peripheral or outlying medical facilities or in emergencies there may be no time to perform complicated neuroimaging. This often results in less accurate placement of probes and other devices within the cranium. For example, when neurosurgery is performed without intraoperative neuronavigation, a surgeon typically has to pass a tube several times into the brain until it is placed into the correct position. Multiple passes to enter the proper position are often needed to correct these errors which increase the risk of bleeding, injury and scarring in the brain.

In view of the lack of availability of intraoperative imaging in many peripheral medical facilities and the lack of time to provide intraoperative imaging in emergencies, a practical tool that enhances accuracy of shunt placement, brain biopsy, and abscess drainage is sorely needed.

BRIEF SUMMARY OF THE INVENTION

The foregoing paragraphs have been provided by way of general introduction and are not intended to limit the scope of the following claims. The described embodiments, together with further advantages, will be best understood by reference to the following detailed description taken in conjunction with the accompanying drawings.

The inventors disclose herein a manual navigation tool that is fast to use and is affordable to both central and peripheral hospitals. It is a useful life-saving tool for emergencies when complex and time consuming neuronavigation is unavailable or impractical. It permits a surgeon to navigate insertion of a probe or other medical instrument into the brain or other parts of the cranium. Navigation is conducted using pre-surgery MRI or CAT scan data to set two angles—a first circumferential angle and a second medial-lateral and/or anterior-posterior angle that in combination allow a surgeon to guide a probe or other instrument along a path toward the target site. In addition to the two angles set on the device to guide the probe or instrument, the probe or instrument may have a measurement scale that indicates the depth of insertion into the cranium along the path defined by the first and second angles. In some embodiments, the probe is equipped with an ultrasonic tip to provide further intraoperative targeting information.

This tool provides accuracy that could be relatively comparable to the more expensive and complex neuronavigation systems. When time and patient condition permit, the accuracy of this manual tool can be stepped up by inclusion of an ultrasound tip or sensors, and even further by concurrent use of fiducial markers corresponding to brain structures.

With the aid of a probe, needle, shunt or other medical instrument, which can be inserted through the cannula (e.g., central channel through the ball) into the cranium, equipped with an ultrasound tip, the manual navigation tool disclosed herein can compensate for intraoperative changes in anatomy. The ultrasound data permits the surgeon to further adjust the position or path of the needle, probe or other device.

Another aspect of the invention is a surgical method using the manual neuronavigation tool disclosed herein, usually after imaging data, for example, CAT or MRI scan data are available. This method may be used for procedures including placement of a ventriculoperitoneal shunt, external ventricular drain placement, brain biopsy, or abscess drainage. As mentioned above, this method is especially useful in an emergency when complex neuronavigation is unavailable or otherwise not feasible.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

These markings align the device to the patient's body. The anterior of the device is anterior towards the nose parallel to the midline. The posterior of the device is posterior towards the occiput parallel to the midline. Medial and lateral trajectories will depend whether the device is on the right side or the left side. Medial is towards the midline of the skull and lateral is always away from the midline of the skull. In imaging, the nose (nasion point) is the reference point anteriorly and the inion (part of the occiput) is the reference point posteriorly. See also FIG. 7C.

Figure 3:
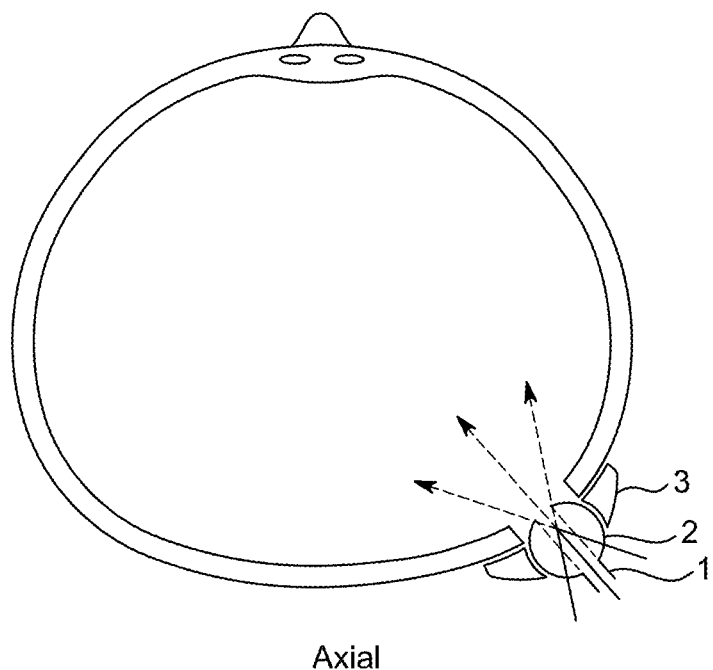

FIG. 3 shows an axial view of the device as positioned over a burr hole in the skull. The arrows show that the cannula of the device can be adjusted over a range of degrees.

Figure 4:
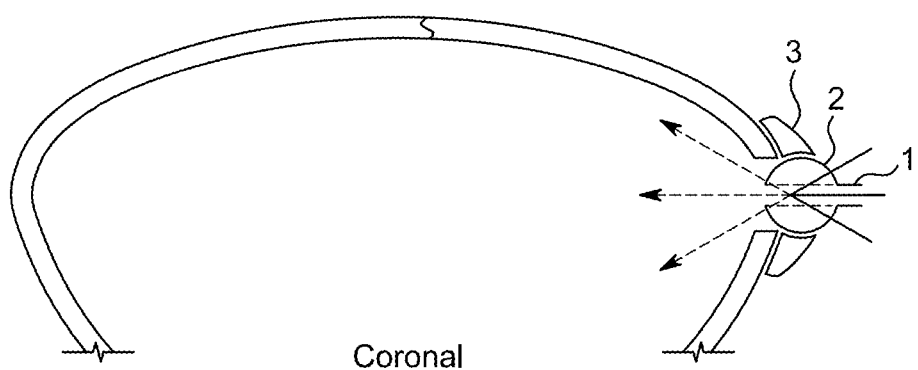

FIG. 4 shows a coronal view of the device as positioned over a burr hole in the skull. The arrows show that the cannula of the device can be adjusted over a range of degrees.

Figure 5:
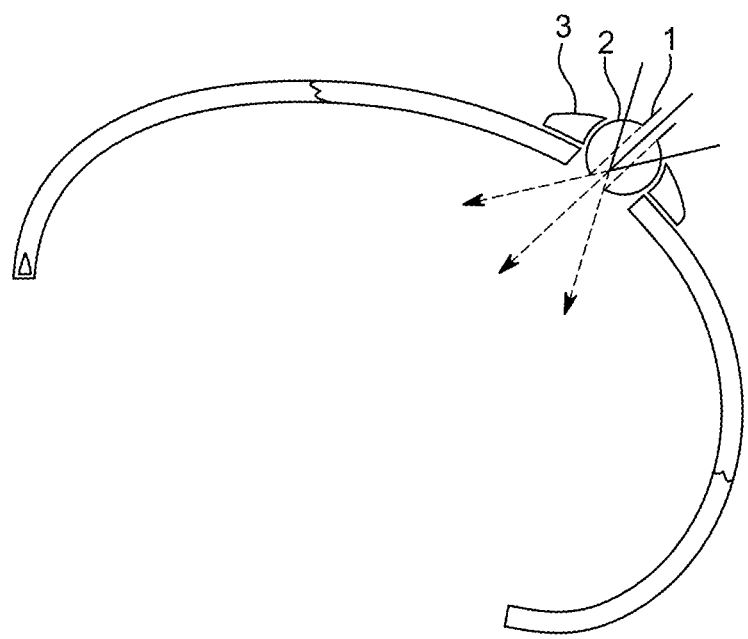

FIG. 5 shows a sagittal view of the device as positioned over a burr hole in the skull. The arrows show that the cannula of the device can be adjusted over a range of degrees.

Figure 6A:
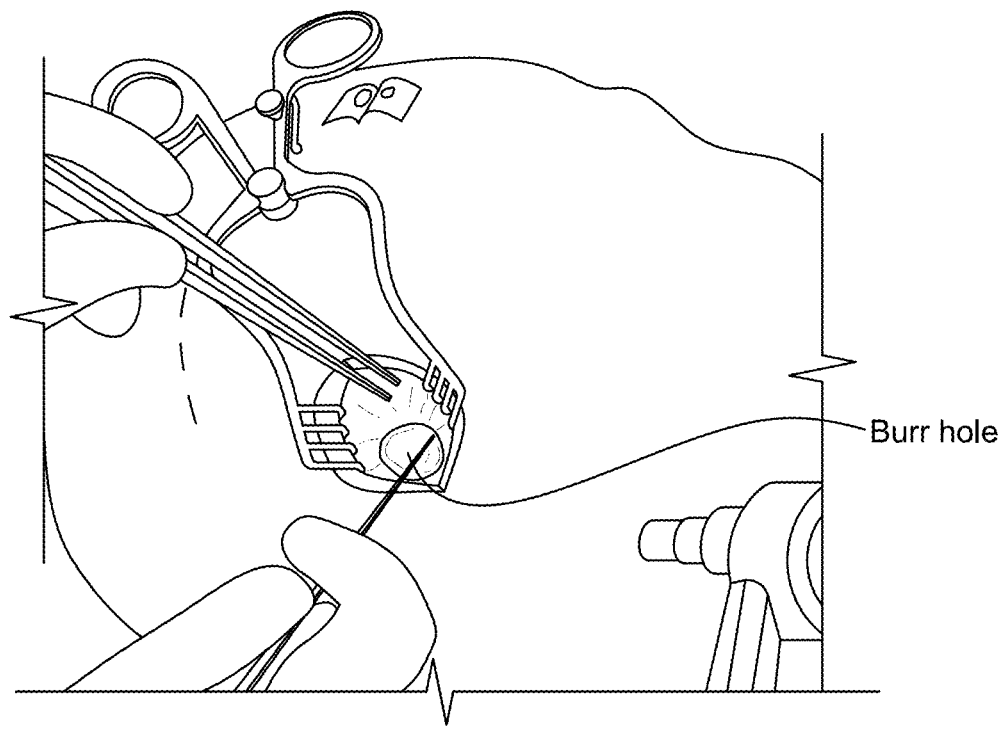

FIG. 6A depicts a burr hole through the skull.

Figure 6B:
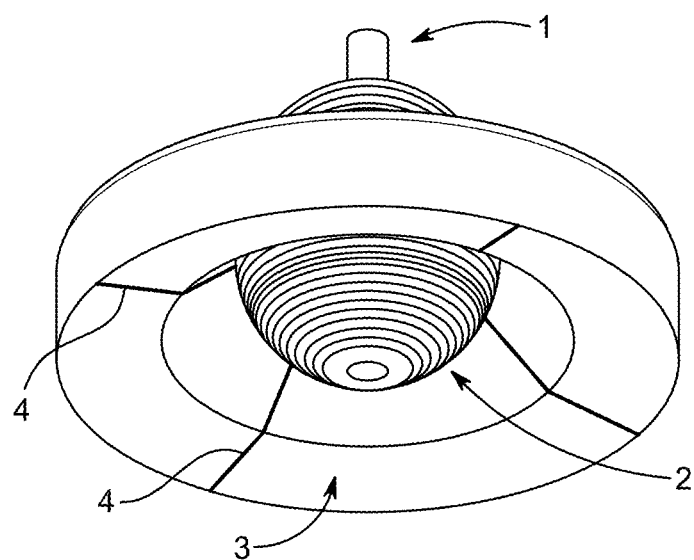

FIG. 6B provides a bottom view of one embodiment of the neuronavigation device showing a lower portion of the ball that fits over the burr hole. Cannula 1, ball 2, frame 3, alignment markings 4, and concentric are shown.

Figure 6C:
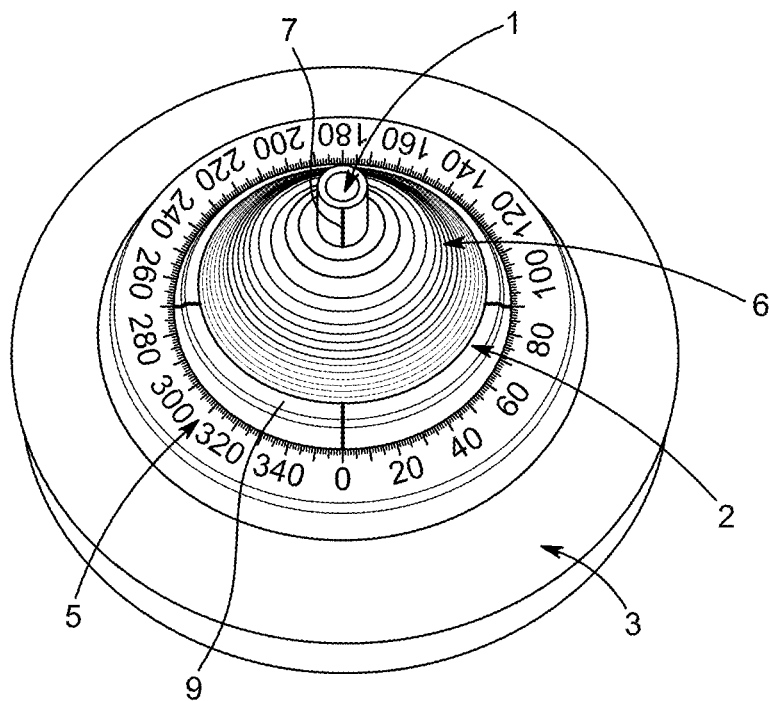

FIG. 6C depicts the top of one embodiment of the device showing cannula 1, ball 2, which comprises concentric protractor markings 6, and frame 3 which comprises alignment markings 4 circumferential protractor markings 5. Cannula 1 has a vertical black cursor 7 which is used to indicate the degree of rotation of the ball around 5. Ball 2 is shown in the vertical position (or position perpendicular to the surface of the head containing the burr hole) with zero degrees of medial-lateral and anterior-posterior tilt. In this embodiment, frame 3 has an upper circular lip 9 which helps seat ball 2 and on which four alignment markings 4 appear.

Figure 6D:
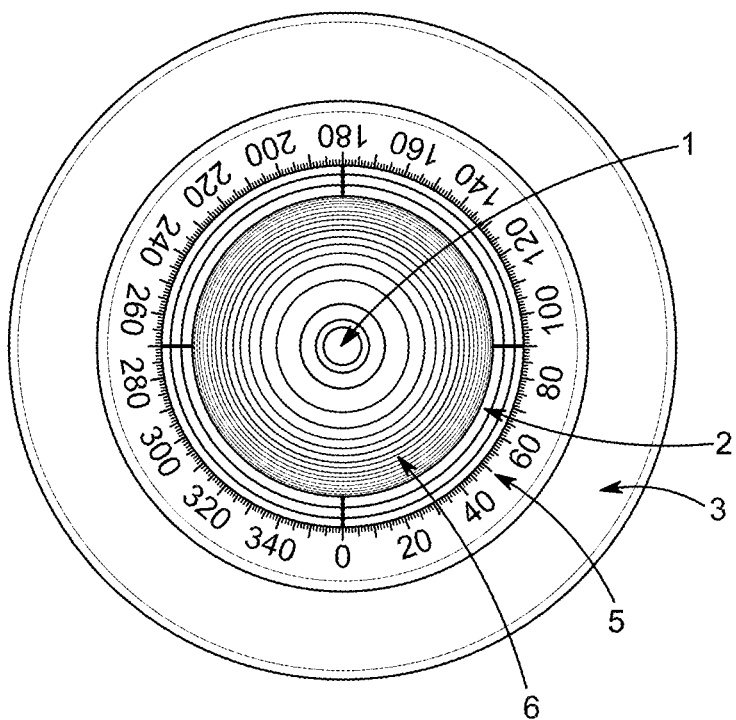

FIG. 6D provides a top view of the device. Cannula 1, ball 2 with concentric protractor markings 6, frame 3 having circumferential protractor markings 5 are shown. Four alignment markers 4 appear on the upper lip of the frame 9.

Figure 6E:
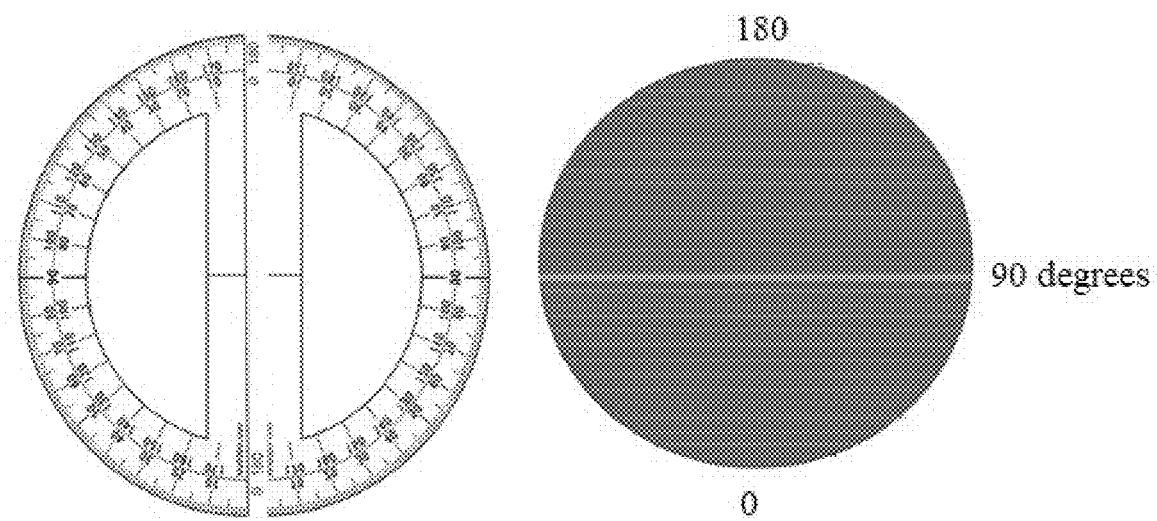

FIG. 6E shows preferred concentric protractor markings for the ball where the concentric circles range from 0 degrees to 180 degrees. Both halves of the ball are numbered from 0-180 degrees. The markings are analogous to those on two protractors facing each other (see left side of this figure). At the equator, the angle is 90 degrees. Moving up from the equator the markings increase to 180 degrees at the top and moving down from the equator decrease to 0 degrees at the bottom.

Figure 7A:
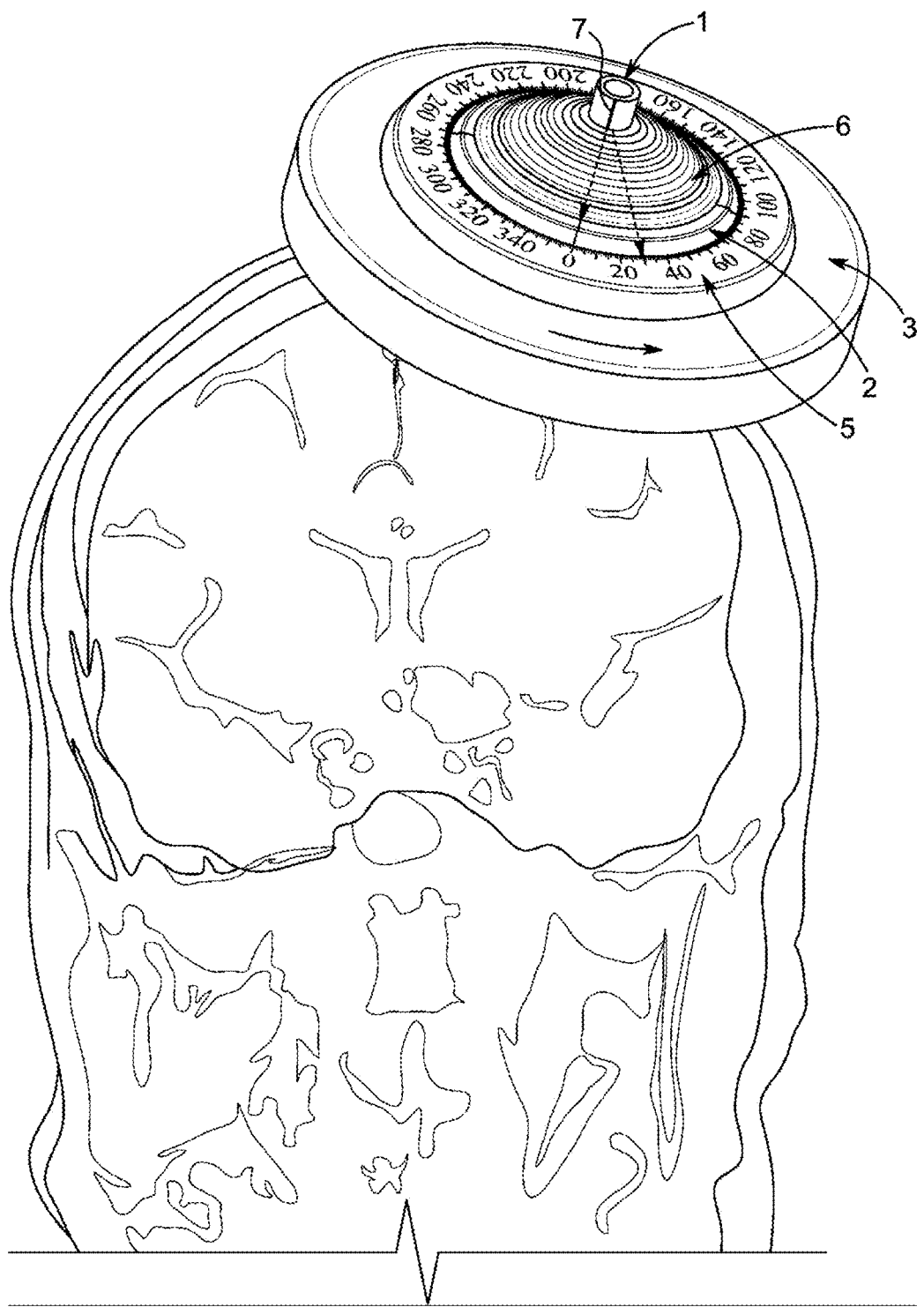

FIG. 7A shows alignment of the device on a parasagittal cranial plane. The arrow indicates the first angle set on the circumferential protractor (here, a 30 degree angle). Cannula 1 with cursor 7, ball 2 with concentric protractor markings 6, and frame 3 with alignment markings 4 and circumferential protractor 5 are shown.

Figure 7B:
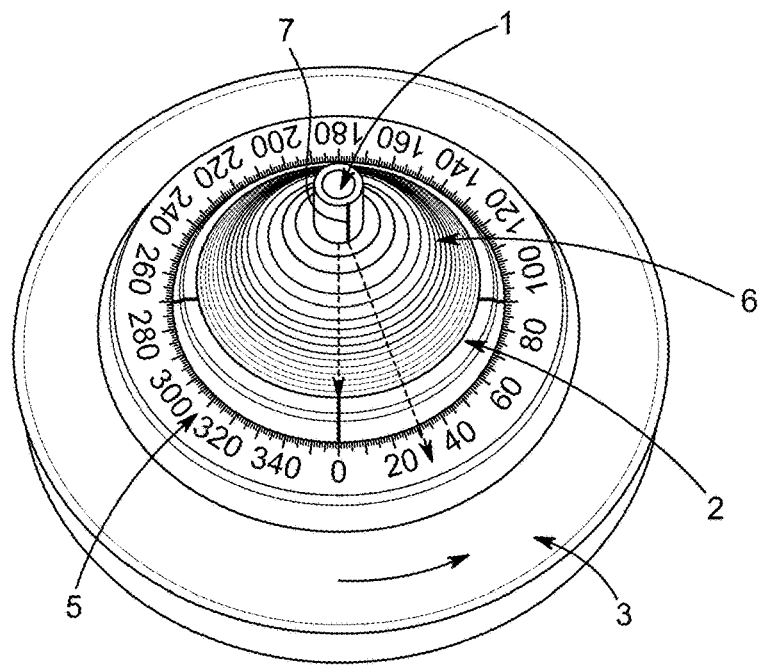

FIG. 7B. A first angle of 30 degrees set on circumferential protractor 5. The second angle has not yet been set on concentric protractor 6 by tilting the ball 2. Cannula 1 with cursor 7, ball 2 with concentric protractor markings 6, and frame 3 with alignment markings 4 and circumferential protractor 5 are depicted.

Figure 7C:
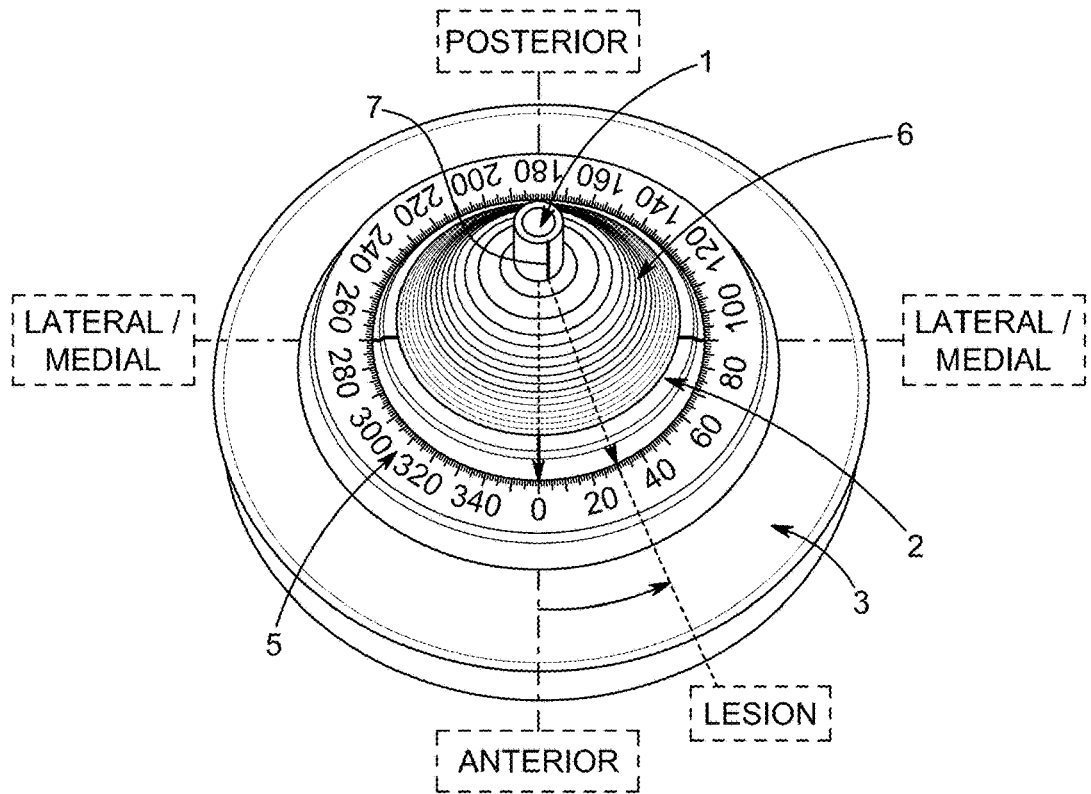

FIG. 7C provides another view of a first angle of 30 degrees targeting a lesion as measured on the circumferential protractor being set and locked in relation to the medial and lateral and anterior and posterior sides of the device. Cannula 1 with cursor 7, ball 2 with concentric protractor markings 6, and frame 3 with alignment markings 4 and circumferential protractor 5 are depicted.

The anterior-posterior axis is fixed. Zero always denotes the anterior and 180 always denotes the posterior. The medial-lateral is not fixed and depends on whether the device is on the right or the left side of the skull. Medial always goes towards the midline of the skull and lateral always goes away from the midline of the skull.

Figure 7D:
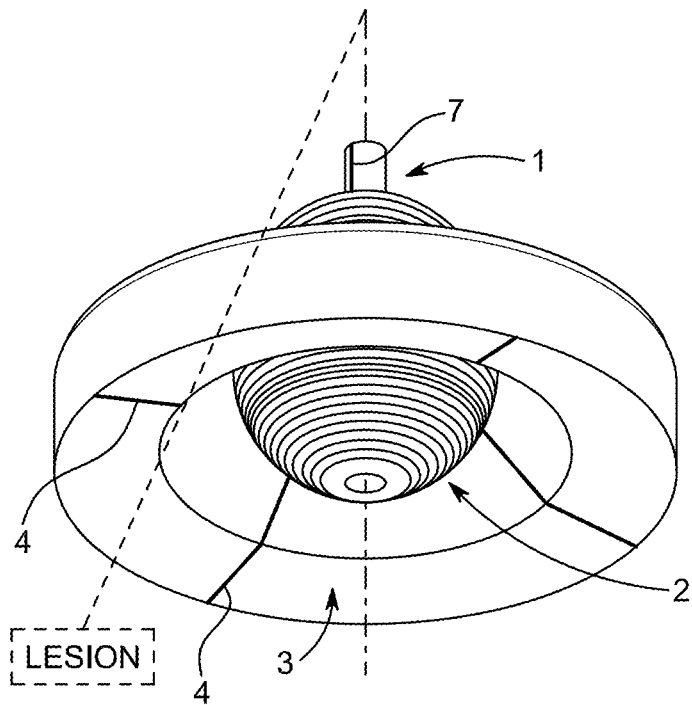

FIG. 7D provides another view of a first angle of 30 degrees targeting a lesion as measured on the circumferential protractor being set and locked in relation to the medial and lateral and anterior and posterior sides of the device. As shown, the second angle which will align the channel in the ball with the lesion has not yet been set. Cannula 1 with cursor 7, ball 2 with concentric protractor markings 6, and frame 3 with alignment markings 4 and circumferential protractor 5 are depicted.

Figure 8A:
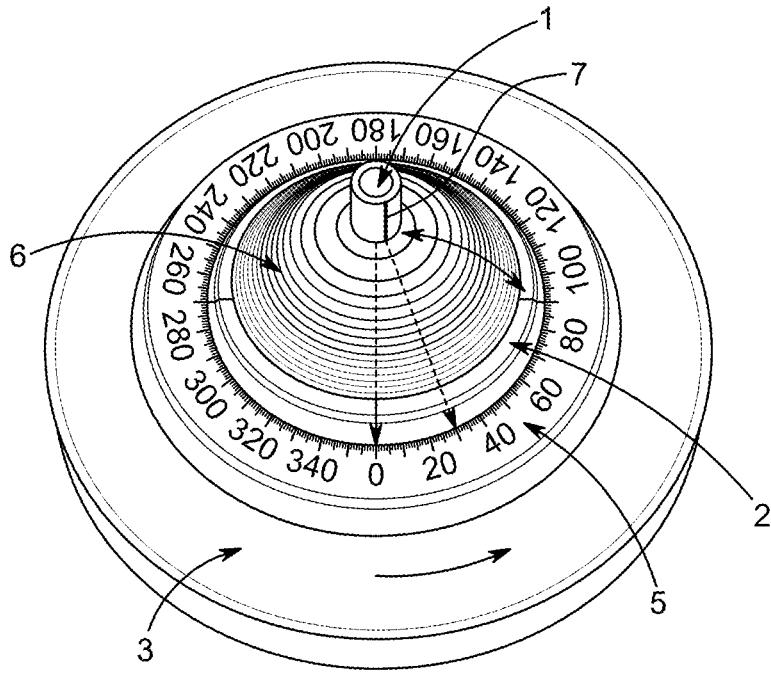

FIG. 8A shows selection and setting of the second angle which in combination with the first angle will target the lesion. The second angle is set by tilting the ball downward so that the channel aligns with the target site (lesion). Cannula 1 with cursor 7, ball 2 with concentric protractor markings 6, and frame 3 with alignment markings 4 and circumferential protractor 5 are depicted.

Figure 8B:
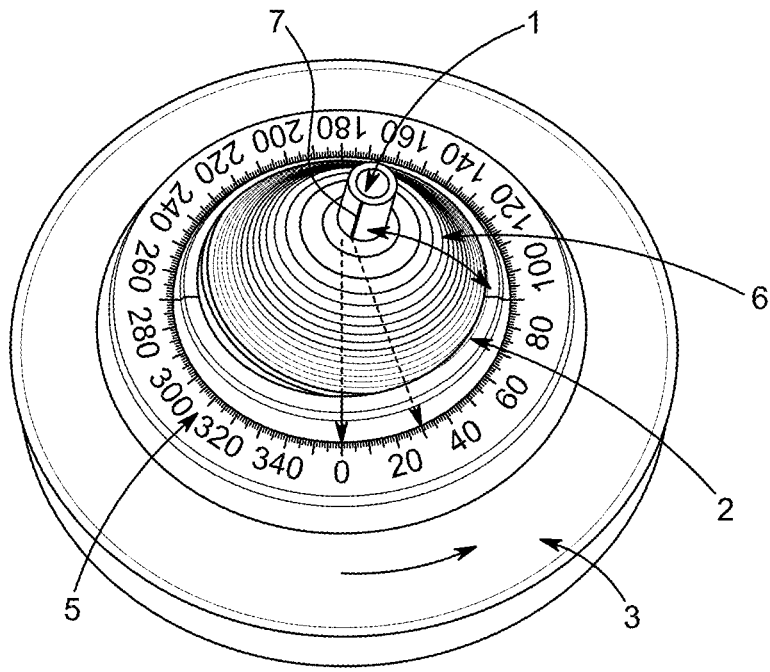

FIG. 8B. Both the 30 degree angle set on the circumferential protractor 5 (see two radial arrows) and the tilt angle ($3^{rd}$ arrow) in combination direct the channel toward the target site. Cannula 1 with cursor 7, ball 2 with concentric protractor markings 6, and frame 3 with alignment markings 4 and circumferential protractor 5 are depicted.

Figure 9A:
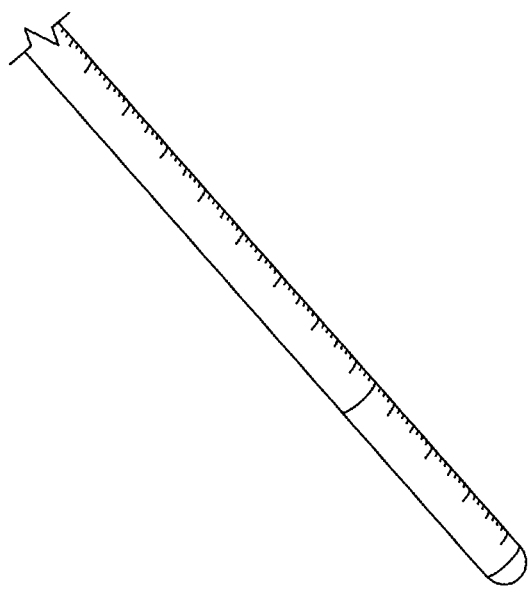
Figure 9B:
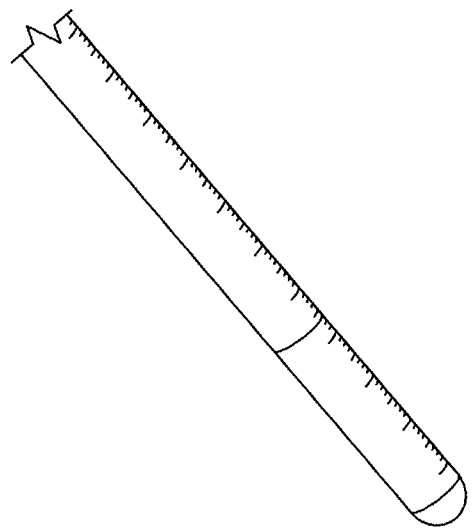

FIGS. 9A and 9B show biopsy probes that are inserted into channel once $1^{st}$ and $2^{nd}$ angles are set and locked. The embodiments of the probes shown have measurement scales to indicate depth of insertion into cranium.

Figure 10A:
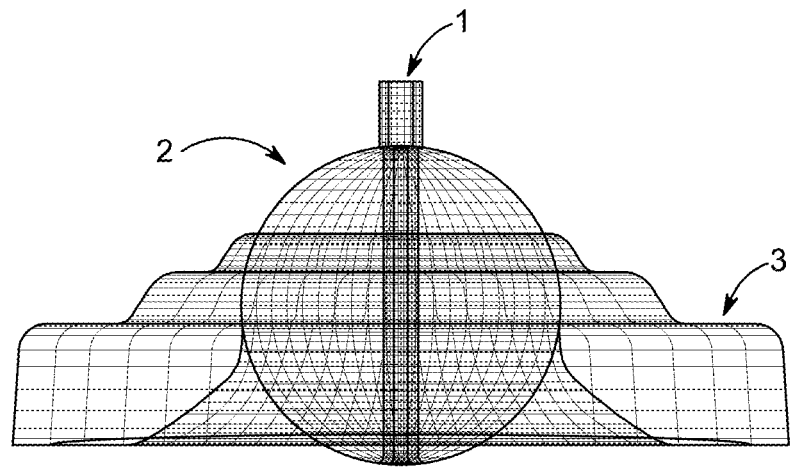
Figure 10B:
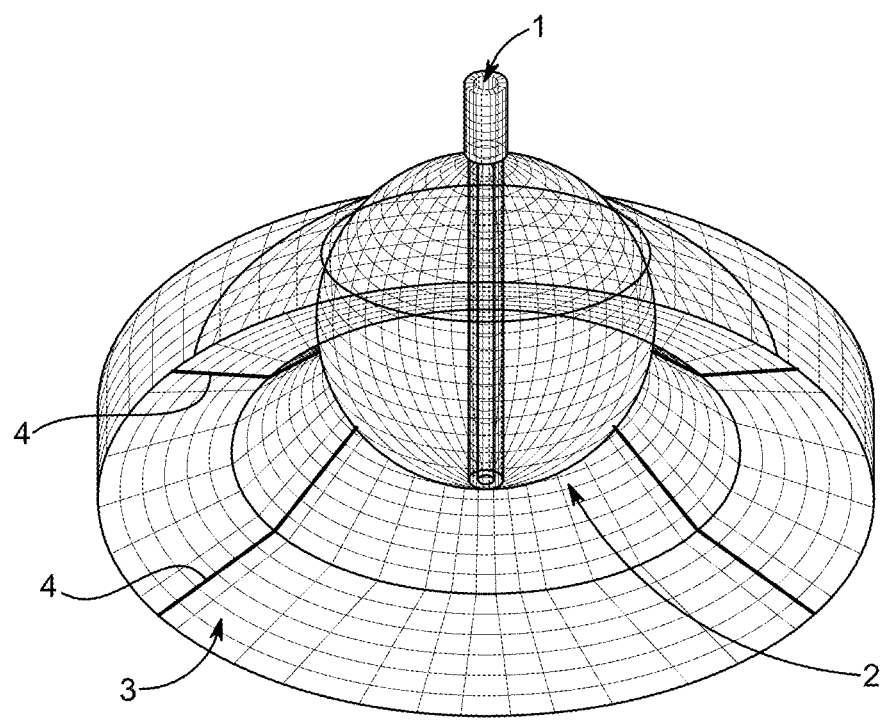

FIGS. 10A-10B shows embodiments of the device having a spheroidal globe. Cannula 1, ball 2, and frame 3 are depicted.

Figure 10C:
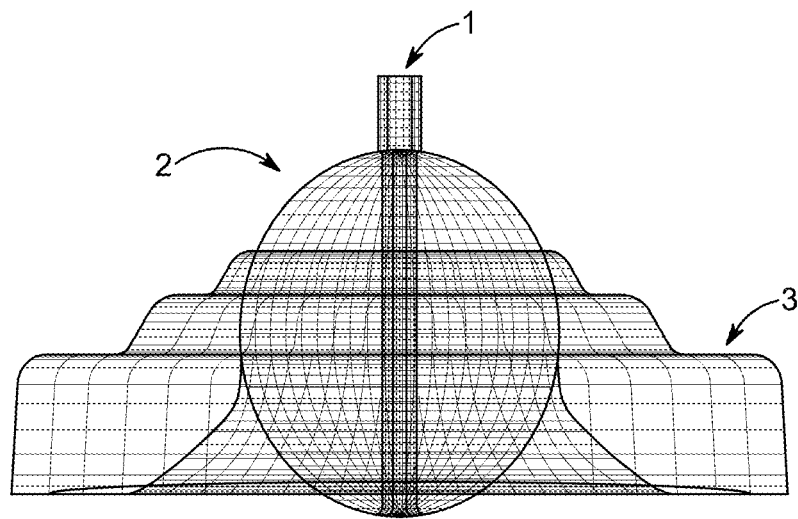
Figure 10D:
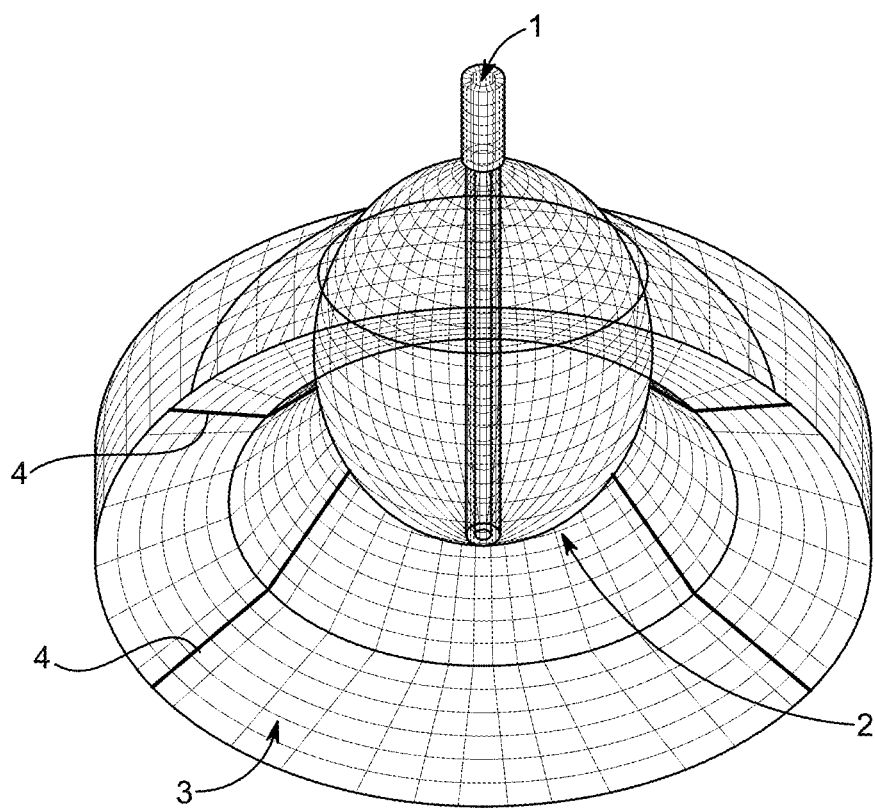

FIGS. 10C-10D show embodiments of the device with an ovoid shape. Cannula 1, ball 2, and frame 3 with alignment markings 4 are depicted.

DETAILED DESCRIPTION OF THE INVENTION

The neuronavigation device disclosed herein is designed to help determine a correct trajectory into the brain or other cranial compartments for passage of a needle, probe, shunt or other medical equipment. Preferably, the device as disclosed herein comprises stainless steel or another material, such as a thermoplastic or metal alloy that can be sterilized.

Initially, a patient's head is imaged, for example, using CAT or MRI imaging, to determine and visualize the location of a target site and to select the best place to drill a burr hole in the patient's skull to permit access to the target site, see FIGS. 3-5 and 6A. The entry point is determined by the surgeon pre-operatively by using the images and correlating it with the fixed anatomical points in relation to the lesion or other target location.

Figure 1:
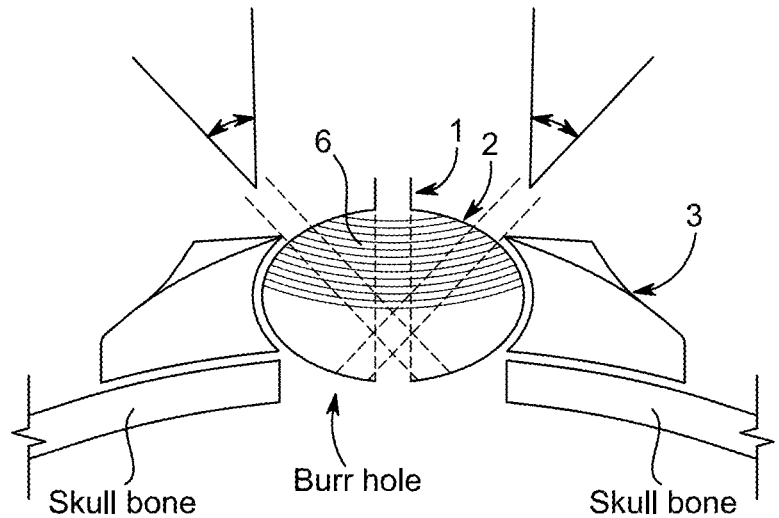
FIG. 1 shows a cross-section of the neuronavigation device having a cannula (fitted within a central channel) 1 through the center of spherical or ellipsoid ball 2 mounted on a curved frame 3 which fits over a burr hole in the skull. The top of the ball comprises regular concentric protractor markings 6 indicate a degree of tilt in a medial-lateral and/or anterior-posterior direction. In this embodiment, the ball may be tilted to align the longitudinal axis of the cannula 1 toward a target site in the cranium. The tilt angle is can range from zero to 180 degrees. Sometimes, the tilt angle can be limited and that can be increased or decreased by moving the sphere up or down or by increasing or decreasing the size of the burr hole.

As shown by FIG. 1, the device comprises linear and radial alignment markings ref. 1 character 4 to permit it to be aligned on the patient's head over a burr hole. This alignment facilitates use of the CT (CAT) or MRI imaging data which are then used to select the first and second angles on the device which direct the cannula 1 of the device toward the target site. In many embodiments, the device is positioned with the alignment markings 4 indicating the posterior and anterior portions of the cranium as shown by FIG. 7A. The device is then placed over, preferably with the ball 2, partially inside of, the burr hole.

To set the first and second angles on the device, which will orient the axis of the cannula 1 of the device when placed over a burr hole toward the target site, the device comprises two sets of protractor markings which help determine an initial circular trajectory (the circumferential protractor markings, see ref character 5 in FIG. 6C and other figures) and a second trajectory in the anterior-posterior and/or medio-lateral dimension using the concentric protractor markings described by reference character 6 in FIG. 6C and other figures and protractor markings as described by FIG. 6E.

Typically, the first angle is set on the circumferential protractor 5 which forms a visible part of frame 3, for example, to a setting deduced from the imaging date. For example, in FIG. 7A, the initial angle is set to 30 degrees. The device is then locked so that the second angle which is set by tilting the ball from its initial position at zero degrees (perpendicular to the surface of the portion of the skull having the burr hole) is set within a plane defined by the initial setting on the circumferential protractor 5. In the example shown by FIG. 7A, the second angle set by tilting the ball 2 would fall within the plane defined by 30 degrees.

Once the first and second angles are both locked immobilizing the ball and cannula in a position oriented toward the target site in the brain, a surgical needle, probe, catheter or other instrument is guided through the cannula 1 toward the target site.

In some embodiments, the surgical needle, probe or other instrument will have measurement markings on it as shown by FIGS. 9A and 9B to help the surgeon determine how deep the needle, probe or other instrument has been inserted into the cranium.

When time and other conditions permit, this method may provide enhanced accuracy of targeting by use of a small ultrasound tip to the needle, probe or other surgical instrument inserted into the cranium. The ultrasonic data obtained from this tip can intraoperatively confirm the proper placement of the needle, probe or other tool in the target site. The ultrasound tip can also be used to re-direct the needle, probe or other surgical instrument during neurosurgery after a procedure which alters the anatomy of the target site, for example, after fluid drainage when the brain tissue shifts due to volumetric changes.

Another feature to further improve accuracy and provide flexibility for repositioning a needle or probe during a surgical procedure, time and conditions permitting, is the addition of one or more sensors. Such sensors can improve the accuracy of the manual methods described herein to be comparable to standard neuronavigation systems. Such sensors are generally applied before performing the imaging and each sensor is applied to a well-known anatomical landmark that correlates anatomically to known intracranial structures. Using data from preoperative imaging and intraoperative sensor data, the appropriate angle required to move a needle, probe, shunt or other medical instrument can be calculated.

Advantages of the methods disclosed herein employing the navigation device include that they do not require complex preparation and take less operative time, and thus improve overall outcomes and hasten patient recovery. The manual navigation device disclosed herein is effective at increasing accuracy and minimizing surgical risks.

The device is also inexpensive compared to more complex conventional navigation devices which often are only affordable by large hospitals or large care centers. Thus, the device as disclosed herein is an excellent choice for hospitals or care facilities in which navigation is not currently economically feasible.

The device as described herein may be used for a variety of different procedures including for intraoperative navigation in hydrocephalus for ventriculoperitoneal shunt or extra-ventricular drain placement; intraoperative navigation for biopsy of deep and small brain lesions; or intraoperative drainage of an abscess/cysts. Navigation with the device decreases the chance of having inconclusive biopsies which is not uncommon as the surgeon might mistakenly take normal adjacent brain tissue instead of the tissue of the lesion itself if the procedure is performed blindly.

Aspects of the invention include, but are not limited to the following embodiments.

A device for inserting a surgical instrument into the brain comprising
- a frame comprising a socket open on its top and bottom ends and which has a flat or convex bottom surface,
- a spherical or ellipsoid ball which can be rotated or tilted within. the socket, wherein the ball has an upper end and a lower end which extend through the top and bottom ends of the socket, and
- a cylindrical cannula through the longitudinal axis of the ball which extends beyond the upper surface of the ball;
- wherein the frame comprises circumferential protractor markings on its top surface around the portion surrounding the socket;
- wherein the surface of the ball comprises concentric latitudinal protractor markings centered on its longitudinal axis, and
- wherein the end of the cannula that extends past the top surface of the ball has a cursor that rotates with the ball and indicates a degree of rotation on the circumferential protractor markings of the frame In another embodiment, a central channel of the ball is fitted with a removable or independent cannula that lines the central channel and which can extend beyond the surface of the ball.

In some embodiments, the cannula through the ball may be integral with the ball. In other embodiments, the cannula will be separate from the ball and can be fitted within a central channel of the ball. In preferred embodiments, the cannula extrudes past the upper surface of the ball. In other embodiments, the cannula may be flush with the upper surface of the ball.

The concentric markings on the ball as protractors in both the anterior-posterior and medial-lateral directions. The degree of tilt will be indicated by the degrees numbered on the concentric lines drawn on the ball, see reference character 6 in the figures which indicates these concentric markings and FIG. 6E which further describes them.

Based on measurements taken from a CT (CAT) or MRI brain scan and on anatomical landmarks, the primary entry point through the skull and into the brain is determined by a surgeon before surgery. The CT and MRI brain scan data are also used to respectively calculate the first angle using the circumferential protractor markings on the frame around the seated ball and the second angle using the concentric protractor markings on the ball itself.

Typically an incision is made at this point and a burr hole is drilled through the skull. The neuronavigation device as disclosed herein is positioned and affixed to the skull over the burr hole. Typically, sutures are used to anchor it to the surrounding soft tissue or through small osteotomies in the skull bone.

Figure 2:
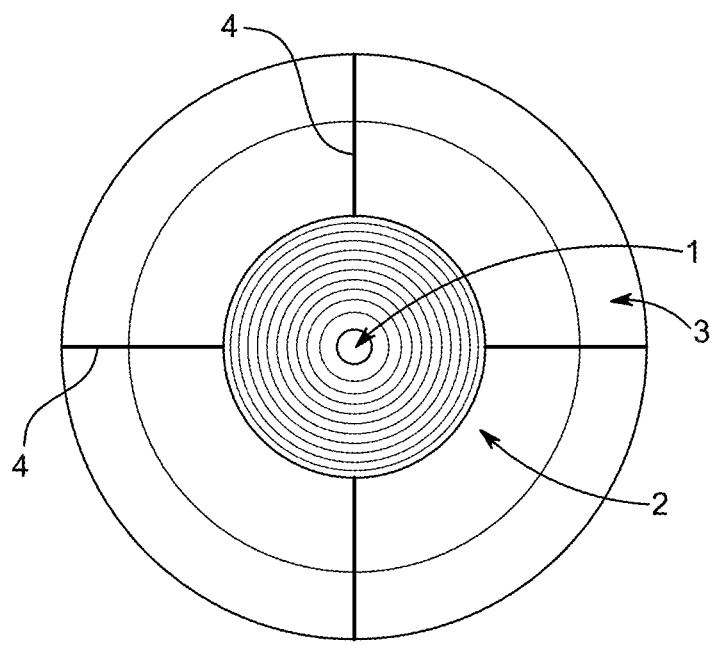
FIG. 2 shows a top view of the device with cannula 1, ball 2 comprising concentric protractor markings 6, and frame 3. The frame comprises four alignment markings 4 which permit the device to be aligned with a sagittal/para-sagittal, coronal/para-coronal plane of a patient's head or with other planes or anatomical landmarks on the head. Reference character 4 shows four fixed markings to align the device when it is applied over the burr hole and fixed to the surrounding soft tissue with stitches or to the bone through osteotomies and stitches.

Reference character number 4 in FIG. 2 which indicates the medial-lateral and posterior-anterior alignments shown in FIG. 7C depicts the fixed markings on the device, they will be used to align the device over the burr holes. The anterior and posterior points are fixed. The anterior mark is aligned anteriorly towards the nose parallel to the midline. The posterior mark will be aligned posteriorly toward the occiput parallel to the midline. In imaging, the nose (nasion point) is the reference point anteriorly and the inion (part of the occiput) is the reference point posteriorly.

In some embodiments, the frame of the device is configured to fit over, or anchor to, or stick to a frontal, parietal, temporal or occipital surface of the head.

As shown by FIG. 1 the inner sides of the frame may be concave so as to form a socket which fits and holds the ball inside the frame and permit its movement. This portion of the frame may be releasable or flexible so as to permit insertion or removal of the ball from the frame. In some embodiments, this part of the frame can be tightened so as to lock the ball in a predetermined angular position.

The height of the frame is typically greater in the center around the hole into which the ball fits. The height of the frame may be taped from a higher point in its center to a lower point at its periphery.

As shown in FIG. 1, the frame may have a concave lower portion which fits over curved portions of the skull.

The frame may have holes to facilitate insertion of screws or other attachments to the head or skull or the portions of the frame contacting the head may be textured to adhere to the head or skull.

During a surgical procedure, the device may be anchored or otherwise secured to the patient's head over a burr hole using various means known in the art.

Preferably, the device has markers on it, such as on the internal part of the frame, which permits it to be aligned with one or more cranial planes or other anatomical landmarks.

The shape, footprint and thickness of the frame may be selected to provide a secure foundation to the portion of the head comprising a burr hole. In a preferred embodiment, the frame is a flat, hollow, cylinder closed on the top and bottom end except for the central socket fitting the ball. The sides of the cylinder range in height from about 1 to 3.5 mm and the diameter of the top surface comprising the central hole ranges from 5 to 15 mm. The central hole is round and has a diameter ranging from about 2 to 7 mm so as to fit the ball. In some embodiments, the frame, ball, or cannula may comprise or be coated with a fluoropolymer, such as with PTFE (Polytetrafluoroethylene), PFA (perfluoroalkoxy alkane), FEP (fluorinated ethylene propylene), ETFE (ethylene tetrafluoroethylene), PVDF (polyvinylidene fluoride), or ECTFE (ethylene chlorotrifluoroethylene) In a preferred embodiment, the height of a central portion of the frame which surrounds the socket tapers to a lesser height at the periphery of the frame.

Preferably, the device as disclosed herein frame has guidelines centered on the cannula that permit it to be manually aligned with at least one cranial plane, such as a sagittal or parasagittal plane, coronal, or axial plane. Examples of such guidelines are shown in FIGS. 6B, 6C and 6D.

The ball, containing the cannula has a shape that permits it to be rotated around its axis and which permits it axis to be tipped in a medial-lateral and/or anterior-posterior direction, preferably, from 0 degrees (axis is vertical as shown in figures, or is perpendicular to the skin surface) to 5, 10, 15, 20, 25, 30, 35, 40, 45, 50, 55, 60, 70, 80, 90, 100, 110, 120, 130 140, 150, 160, 170 to 180 degrees or any intermediate value or values within this range. In a preferred embodiment, the ball is substantially spherical. In other embodiments, for example, as shown by FIG. 10C or 10D, the ball is egg-shaped or ellipsoid.

In some embodiments, the cannula of the ball which has a cursor or mark that rotates with the ball and indicates an angle of circumferential rotation with respect to the circumferential protractor markings on the frame. An example of such a cursor is shown in FIG. 6C where it is located on a cylindrical portion of the cannula extruding from the ball.

The top, visible part of the frame around the ball and socket may be a flat, ringed shaped area comprising the circumferential protractor. This part of the frame preferably has four alignment or cursor markings spaced apart by 90 degrees, such as those shown by FIGS. 6C and 6D.

In preferred embodiments the position of the ball in the socket can be locked at a particular circumferential angle or at a particular degree of tilt in an anterior-posterior or medial lateral direction.

One skilled in the art may select an appropriate type of socket to hold the ball and an appropriate locking mechanism for holding the ball at a predetermined angular position. Examples of locking mechanisms include ball locks, locking rings, twist locks, locking levers, and locking pins. In another embodiment, tightness of the ball inside of the socket permits movement of the ball only when sufficient force is applied, for example, via manual movement of the ball via an extended end of the cannula. Thus, the ball may be forcefully placed into a predetermined angular position in which it remains during neurosurgery. Preferably, twist locks are used to lock the ball in a particular position.

In some typical embodiments the ball can be tilted to orient the cannula from 0, 5, 10, 15, 20, 25, 30, 35, 40, 45, 50, 55, 60, 70, 80, 90, 100, 110, 120, 130 140, 150, 160, 170 to 180 degrees degrees, wherein at 0 degrees the cannula is substantially perpendicular to the surface of the head around the burr hole.

After the first and second angles are selected based on the imaging data, the position of the ball is typically locked. Typically, the cannula in the ball is configured to pass into the brain a surgical shunt, catheter, needle, fine biopsy needle, probe, and biopsy probe. In some embodiments, the probe may extend outward via a cylindrical projection from the surface of the ball up to about <2, 2, 5, 10, 15 or >20 mm.

In some embodiments, the frame, ring between the frame and ball, ball and cannula may be configured so that they can be disassembled and reassembled, for example, for cleaning, lubrication, or adjustment between uses. In some embodiments the different components of the device are lubricated, for example with oil, such as a mineral oil or synthetic oil, or a solid lubricant such as graphite.

Typically, each element of the device can be sterilized. Preferably, each element of the device is made of material that can be heat or steam sterilized, for example, in an oven or autoclave, sterilized with radiation, or which are stable under conditions of low temperature sterilization such as with ethylene oxide gas hydrogen peroxide gas plasma, peracetic acid immersion, or ozone).

In a preferred embodiment, the frame is substantially circular and has a diameter ranging from 20-25 mm for adults and 15-20 mm for children and a thickness or height ranging from 2 to 12 mm, the ball has an equatorial diameter ranging from 14 mm in adults and 10-12 mm in children and a length along its longitudinal axis ranging from 2 to 12 mm, and the cannula has a diameter ranging from 1 to 5 mm and a length ranging from 5 to 20 mm. The cannula may extend past the surface of the ball, for example, the channel may comprise a cylindrical tube which extends through the channel and outward past the surface of the ball and which helps guide or thread medical instruments or materials through the cannula into the brain other target inside the skull or which helps manually adjust the angular position of the ball. In some embodiments, the frame is a solid flat cylindrical structure and has a bottom side through which the lower portion of the ball extends. The frame, ball, or cannula optionally, may have at least one surface lined with polyfluoroethylene or another fluoropolymer. Usually the average adult burr hole size is 16 mm and average child burr hole size is 11-14 mm, the frame diameter is at least 16 mm. the ball is slightly smaller than the burr hole size by about 2 mm. for example, for adults, the ball can be 14 mm and in children 10-12 mm.

In some embodiments, the frame, ball and/or cannula comprise stainless steel. In other embodiments, the device or its component parts may comprise a thermoplastic that can be sterilized. In other embodiments, the frame further comprises a lip, flange, bracket or other surface through which it can be attached or anchored to the skull. In other embodiments, an adhesive or adhesive pad may be used to attach the device to the head.

Another embodiment of the invention is directed to kit or system comprising the device as disclosed herein and at least one sterile surgical shunt, catheter, catheter, needle or probe. Several instruments can be inserted through the cannula, a biopsy needle is provided with a kit. The shunts and brain needles are parts of the basic tools available in any peripheral health care center in which a neurosurgeon operates. The dimensions are well known and can easily fit within the cylindrical cannula of the embodiment.

In some embodiments, the kit will further comprise a surgical instrument having an ultrasonic tip for intraoperative ultrasonic imaging or guidance. The kit may also contain one or more sensors suitable for installation over anatomical landmarks that correspond to intercranial structures.

Another aspect of the invention is directed to a method for guiding a surgical tool into the brain of a patient comprising imaging a target position in the brain of the patient, producing a burr hole through the skull of the patient, seating a lower end of the cannula of the device of in or above the burr hole, rotating the ball and cursor to a first angle of the target site as determined from the said imaging and as measured on the circumferential protractor on the frame, locking the ball at this angle so that the ball does not rotate in the central cavity, tilting the ball comprising the cannula to a second angle toward the target site as determined from said imaging and as measured on the concentric latitudinal protractor markings on the ball, locking the ball at this second angle so that the ball no longer tilts, and inserting the surgical tool through an exterior end of the channel, through the channel into the target site in or around the brain.

In some embodiments, the said patient is in need of an intraoperative ventriculoperitoneal shunt and wherein said method further comprises positioning and placing the shunt. In other embodiments the patient is in need of external ventricular drain placement and the method further comprises positioning and placing the drain. In still other embodiments the patient is in need of a brain biopsy and the method further comprises taking a brain biopsy. In other embodiments, the target site is in a brain abscess and the method further comprises draining the abscess.

In further embodiments, the surgical tool further comprises an ultrasonic tip and said method further comprises refining a path of the surgical tool using data from ultrasonography;

In other embodiments, the method further comprises placing one or more sensors on the head of the patient corresponding to anatomical landmarks and further comprising refining a path of the surgical tool using data from the sensors.

Terminology. Terminology used herein is for the purpose of describing particular embodiments only and is not intended to be limiting of the invention.

As used herein, the singular forms "a", "an" and "the" are intended to include the plural forms as well, unless the context clearly indicates otherwise.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise. For example, the device as disclosed herein has a top surface, which when positioned on the head of a patient would be distal to the patient's head. Similarly, the bottom surface of the device would be proximal to the patient.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A device for inserting a surgical instrument into the brain of a patient requiring neurosurgery, comprising:
 a frame comprising a socket open on its top and bottom ends and which has a flat or convex bottom surface, wherein the socket defines a circumference of the frame;
 a spherical or ellipsoid ball which can be rotated or tilted within the socket, wherein the ball has an upper end and a lower end which extend through the top and bottom ends of the socket, wherein a bottom surface of the ball is in continuous circumferential contact with the frame, and the frame is configured for contact with a skull of the patient requiring neurosurgery around the circumference of the frame; and
 a cylindrical cannula through the longitudinal axis of the ball which extends beyond the upper surface of the ball;
 wherein the frame comprises circumferential protractor markings on a top surface around the socket;
 wherein the top and bottom surfaces of the ball comprise concentric latitudinal protractor markings centered on a longitudinal axis of the ball, and wherein the concentric latitudinal protractor markings are evenly spaced apart from each other across the entire surface of the ball, and
 wherein the end of the cannula that extends past the top surface of the ball has a cursor that rotates with the ball and indicates a degree of rotation on the circumferential protractor markings of the frame.

2. The device of claim 1, wherein a height of a central portion of the frame which surrounds the socket tapers to a lesser height at the periphery of the frame.

3. The device of claim 1, further comprising a lock which immobilizes the ball within the socket.

4. The device of claim 1, wherein a lower surface of the frame has anchors to secure the frame to the head of the patient.

5. The device of claim 1, wherein the frame comprises four radial linear markings on its upper or lower surface spaced 90 degrees apart around the circumference of the socket.

6. The device of claim 1, wherein the socket is configured so that the ball can be tilted to orient the cannula, wherein at 0 degrees the cannula is perpendicular to the surface of the head of the patient.

7. The device of claim 1, wherein the cannula has a diameter ranging from 1 to 5 mm and, optionally, may have an inner surface lined with polyfluoroethylene or another fluoropolymer.

8. The device of claim 1, wherein the frame is substantially circular and has a diameter ranging from 18-28 mm, the ball has an equatorial diameter ranging from 10-14 mm and a length along its longitudinal axis ranging from 2 to 12 mm, and the cannula has a diameter ranging from 1 to 5 mm and a length ranging from 5 to 20 mm.

9. The device of claim 1, wherein the frame, ball and/or cannula comprises stainless steel and optionally has at least one surface lined with polyfluoroethylene or another fluoropolymer.

10. The device of claim 1, wherein a lower part of the frame further comprises a lip, flange, bracket or other surface by or through which it can be attached or anchored to the skull.

11. A kit or system comprising the device of claim 1 and at least one sterile surgical shunt, catheter, needle or probe.

12. The kit or system of claim 11, wherein the shunt, catheter, needle or probe further comprises an ultrasonic tip.

13. The kit of system of claim 11, further comprising one or more sensors suitable for installation on anatomical landmarks that correspond to intercranial structures.

14. The device of claim 1, further comprising an upper circular lip having four radial alignment markings distributed 90 degrees apart from one another, wherein the upper circular lip is configured to seat the spherical or ellipsoid ball within the socket, and wherein the upper circular lip is in direct circumferential contact with an upper surface of the spherical or ellipsoid ball.

15. The device of claim 1, wherein the top surface of the frame is in the form of a stair step structure comprising a first stair step structure, a second stair step structure vertically stacked on the first stair step structure, and a third stair step structure vertically stacked on the second stair step structure; wherein the second stair step structure comprises the circumferential protractor markings; and wherein the third stair step structure represents the upper circular lip.

16. The device of claim 15, wherein a first height of the first stair step structure is longer than a second height of the second stair step structure, and the second height of the second stair step structure is longer than a third height of the third stair step structure; and wherein a height is defined as the vertical distance between the two closest stair step structures.

17. The device of claim 1, wherein the ball is in the form of a sphere having an upper hemisphere and a lower hemisphere meeting at an equator of the sphere, wherein the top surface of the ball is an outer surface of the upper hemisphere and the lower surface of the ball is an outer surface of the lower hemisphere.

* * * * *